United States Patent
Gliner et al.

(10) Patent No.: US 10,603,472 B2
(45) Date of Patent: Mar. 31, 2020

(54) GUIDEWIRES HAVING IMPROVED MECHANICAL STRENGTH AND ELECTROMAGNETIC SHIELDING

(71) Applicants: Biosense Webster (Israel) Ltd., Yokneam (IL); Acclarent, Inc., Irvine, CA (US)

(72) Inventors: Vadim Gliner, Haifa (IL); Assaf Govari, Haifa (IL); Ghislain G. Sema, Costa Mesa, CA (US)

(73) Assignees: Biosense Webster (Israel) Ltd., Yokneam (IL); Acclarent, Inc., Irvine, CA (US)

( * ) Notice: Subject to any disclaimer, the term of this patent is extended or adjusted under 35 U.S.C. 154(b) by 95 days.

(21) Appl. No.: 15/334,175

(22) Filed: Oct. 25, 2016

(65) Prior Publication Data
US 2018/0110965 A1 Apr. 26, 2018

(51) Int. Cl.
*A61M 25/09* (2006.01)
*A61B 5/06* (2006.01)
*A61B 5/00* (2006.01)

(52) U.S. Cl.
CPC ............. *A61M 25/09* (2013.01); *A61B 5/065* (2013.01); *A61B 5/6851* (2013.01); *A61M 2025/0915* (2013.01); *A61M 2025/09066* (2013.01); *A61M 2025/09108* (2013.01); *A61M 2025/09133* (2013.01); *A61M 2025/09166* (2013.01); *A61M 2025/09175* (2013.01)

(58) Field of Classification Search
CPC ........ A61M 25/09; A61M 2025/09066; A61M 2025/09108; A61M 2025/09133; A61M 2025/09166; A61M 2025/09175; A61M 2025/0915; A61B 5/065; A61B 5/6851
See application file for complete search history.

(56) References Cited

U.S. PATENT DOCUMENTS

| | | | |
|---|---|---|---|
| 5,269,757 A | 12/1993 | Fagan et al. | |
| 5,391,199 A | 2/1995 | Ben-Haim | |
| 5,876,356 A * | 3/1999 | Viera | A61L 31/022 600/585 |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |

(Continued)

FOREIGN PATENT DOCUMENTS

| | | |
|---|---|---|
| WO | WO 96/05768 A1 | 2/1996 |
| WO | WO 02/19928 A2 | 3/2002 |

OTHER PUBLICATIONS

European Search Report, Extended, and Written Opinion dated Mar. 15, 2018 for Application No. EP 17198100.4, 7 pgs.

*Primary Examiner* — Devin B Henson
(74) *Attorney, Agent, or Firm* — Frost Brown Todd LLC

(57) ABSTRACT

A medical guidewire includes a flexible spiral coil, a fiber, and a strengthening element. The coil is configured to guide a medical device into a patient body. The fiber extends along at least part of the coil, is coupled to the at least part of the coil at one or more first predefined locations and is configured to mechanically strengthen the at least part of the coil. The strengthening element is coupled to one or more second predefined locations along a distal section of the coil, and is configured to mechanically strengthen the distal section.

18 Claims, 2 Drawing Sheets

(56) References Cited

U.S. PATENT DOCUMENTS

| | | | |
|---|---|---|---|
| 6,690,963 B2 | 2/2004 | Ben-Haim et al. | |
| 7,532,920 B1 | 5/2009 | Ainsworth et al. | |
| 7,540,845 B2 * | 6/2009 | Parins | A61M 25/09 600/585 |
| 7,729,742 B2 | 6/2010 | Govari | |
| 7,833,175 B2 | 11/2010 | Parins | |
| 7,881,807 B2 | 2/2011 | Schaer | |
| 8,182,432 B2 | 5/2012 | Kim et al. | |
| 9,095,685 B2 * | 8/2015 | Sela | A61B 5/06 |
| 2004/0068178 A1 | 4/2004 | Govari | |
| 2004/0167436 A1 * | 8/2004 | Reynolds | A61M 25/09 600/585 |
| 2004/0167442 A1 * | 8/2004 | Shireman | A61M 25/09 600/585 |
| 2008/0045908 A1 * | 2/2008 | Gould | A61M 25/09 604/272 |
| 2010/0191150 A1 * | 7/2010 | Palme, Jr. | A61M 25/09 600/585 |
| 2011/0060316 A1 | 3/2011 | DiCarlo | |
| 2012/0197246 A1 | 8/2012 | Mauch | |
| 2016/0007842 A1 | 1/2016 | Govari et al. | |
| 2017/0239450 A1 * | 8/2017 | Kocaturk | A61M 25/09 |

\* cited by examiner

GUIDEWIRES HAVING IMPROVED MECHANICAL STRENGTH AND ELECTROMAGNETIC SHIELDING

FIELD OF THE INVENTION

The present invention relates generally to medical guidewires, and particularly to methods and apparatus for improving mechanical and electromagnetic shielding properties of medical guidewires.

BACKGROUND OF THE INVENTION

Guidewires are used for guiding medical devices of various types, such as sinuplasty balloons, into a patient body for applying some medical procedure. Various guidewire configurations are known in the art.

For example, U.S. Pat. No. 8,182,432, whose disclosure is incorporated herein by reference, describes a guidewire for use in ear, nose and throat procedures. The guidewire may include an elongate core wire having a proximal region and a distal region. The distal region of the core wire may include a flattened portion adapted to provide preferential flexure along at least one axis of the wire. The distal region of the core wire may include a tip portion distal of the flattened portion, wherein at least one cross-sectional dimension of the tip portion is greater than at least one cross-sectional dimension of the flattened portion. The guidewire may include an outer coil disposed around at least a portion of the elongate core wire.

European Patent EP1315460, whose disclosure is incorporated herein by reference, describes an elongate tubular body that extends between a rotatable cutter and a control. The cutter is connected to the control with a rotatable element. Vacuum is applied through an annular passage defined between the tubular body and the rotatable element. The tubular body has a sufficiently small outside diameter, and sufficient kink resistance and pushability to navigate through the internal carotid artery and at least into the M3 segment of the middle cerebral artery.

U.S. Patent Application Publication 2016/0007842, whose disclosure is incorporated herein by reference, describes apparatus, including a guidewire having a distal end, which is configured to be inserted into proximity with a nasal sinus of a patient, the guidewire having a lumen. The apparatus also includes an optic fiber, traversing the lumen, configured to illuminate the distal end, and a coil, wound around the optic fiber and located within the lumen at the distal end, configured to generate a signal in response to a magnetic field interacting with the coil. A processor is configured to receive the signal and to evaluate a location of the distal end in response to the signal.

SUMMARY OF THE INVENTION

An embodiment of the present invention that is described herein provides a medical guidewire including a flexible spiral coil, a fiber, and a strengthening element. The coil is configured to guide a medical device into a patient body. The fiber extends along at least part of the coil, is coupled to the at least part of the coil at one or more first predefined locations and is configured to mechanically strengthen the at least part of the coil. The strengthening element is coupled to one or more second predefined locations along a distal section of the coil, and is configured to mechanically strengthen the distal section.

In some embodiments, the coil includes a position sensor coupled to the distal section. In other embodiments, the strengthening element includes an electrically-conductive material, and is further configured to provide electromagnetic shielding that reduces electromagnetic interference to measurements of the position sensor. In yet other embodiments, the position sensor is configured to sense signals in a first frequency range, and the strengthening element is configured to pass the signals in the first frequency range, and to reduce the electromagnetic interference in a second frequency range that is different from the first frequency range.

In an embodiment, the strengthening element includes a biocompatible material. In another embodiment, the fiber is coupled to an inner surface at the first predefined locations of the coil. In yet another embodiment, at least a first location among the first predefined locations is identical to a second location among the second predefined locations, and the strengthening element is configured to couple the fiber to the at least part of the coil at the first location. In some embodiments, the strengthening element includes a hypo-tube. In other embodiments, the fiber is made from vectran.

There is additionally provided, in accordance with an embodiment of the present invention, a method for producing a medical guidewire, including providing a flexible spiral coil for guiding a medical device into a patient body. A fiber that mechanically strengthens the at least part of the coil is extended along at least part of the coil, and is coupled to the at least part of the coil at one or more first predefined locations. A strengthening element is coupled to one or more second predefined locations along a distal section of the coil for mechanically strengthening the distal section.

The present invention will be more fully understood from the following detailed description of the embodiments thereof, taken together with the drawings in which:

DETAILED DESCRIPTION OF EMBODIMENTS

Overview

Figure 1:
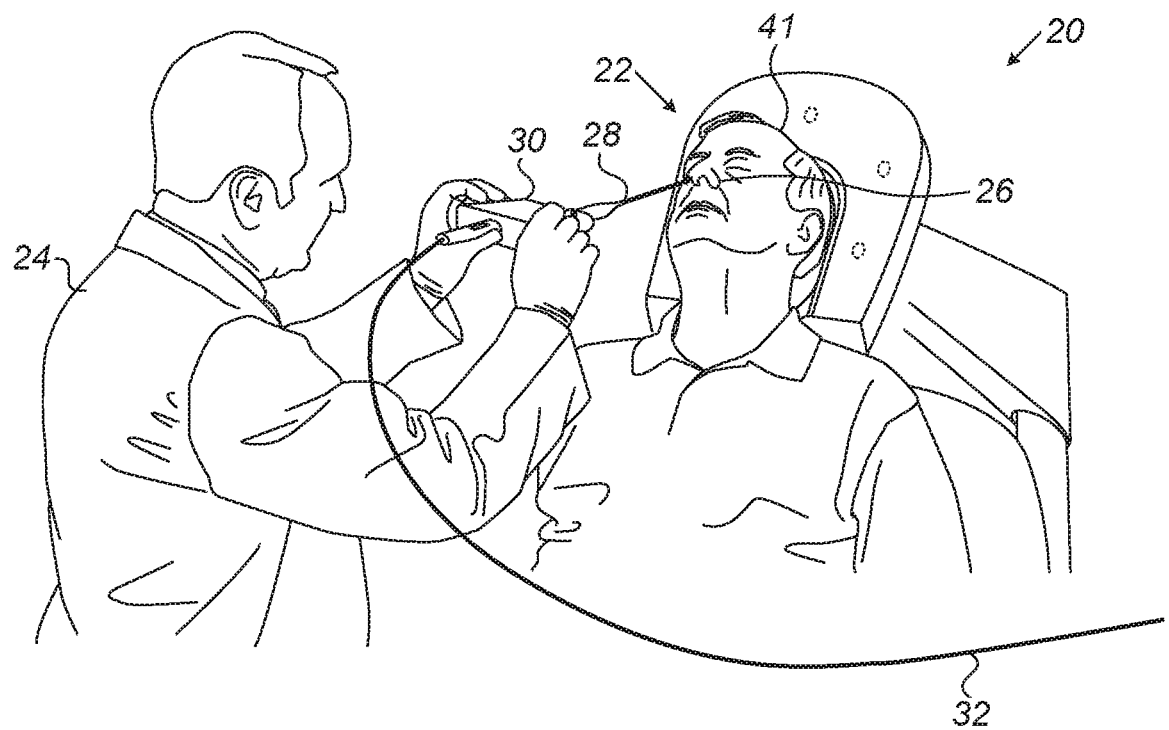
FIG. 1 is a schematic, pictorial illustration of a sinuplasty surgical system, in accordance with an embodiment of the present invention.

Medical guidewires are used for guiding medical devices into a patient body in a variety of applications. For example, in a sinuplasty procedure carried out in the ear-nose-throat (ENT) system of the patient, a physician first inserts a guidewire through the patient nose and navigates the distal end of the guidewire to a target location in the ENT system. After positioning the distal end at the target location, the physician guides a medical device to the target location along the guidewire. After concluding the sinuplasty procedure, the physician retracts the medical device and the guidewire out of the patient body.

In practice, during the navigation and/or retraction of the guidewire, the physician may apply high mechanical (e.g., tensile) forces that may deform the guidewire. A deformation caused to the cross section shape of the guidewire at some point may block the guided device from passing through that point, and may also degrade the accuracy of assessing the position of the distal end of the guidewire.

Embodiments of the present invention that are described hereinbelow provide techniques for making the guidewire less vulnerable to deformation by improving its mechanical strength. In the disclosed embodiments, the guidewire comprises a flexible spiral coil, which is configured to guide the medical device to the target location.

In some embodiments, a fiber made of Vectran™ extends along a distal section of the guidewire and is coupled to the coil by gluing the fiber to the inner surface of the coil at predefined locations along the distal section. The vectran fiber has a tensile strength of about 3 giga-pascal (GPa). Using such a fiber, having a diameter of 15-20 microns, improves the mechanical strength of the coil by a factor of about 10, without compromising the guidewire flexibility, which is important for navigating the guidewire through bent cavities of the body.

In some embodiments, a strengthening element may be coupled to one or more predefined locations along the distal section, so as to further strengthen the distal section of the guidewire. The strengthening element may comprise, for example, adhesive material, solder material or a hypo tube.

In an embodiment, a position sensor of a magnetic position tracking system is fitted at the distal section of the guidewire, for assisting the physician in navigating the distal end of the guidewire to the target location. The position sensor is configured to sense magnetic fields produced by field generators of the position tracking system. In some embodiments, the strengthening element at the distal section is electrically conductive, and also serves to shield the position sensor from electromagnetic interference that may degrade the measurement accuracy of the distal end position.

The disclosed techniques enable the physician to guide the medical device along the guidewire to the target location safely and accurately by retaining the shape and flexibility of the guidewire, and by blocking undesired electromagnetic interference from interfering with the position sensor operation. Furthermore, the disclosed techniques may save operational costs by enabling the physician to reuse the same guidewire and the position sensor in multiple sinuplasty procedures.

System Description

FIG. 1 is a schematic, pictorial illustration of a sinuplasty surgical system 20, in accordance with an embodiment of the present invention. In some embodiments, system 20 comprises an ear-nose-throat (ENT) guidewire 28, which is configured to guide any suitable ENT medical device, such as a sinuplasty balloon (not shown), to a target location in an ENT system of a patient 22.

In an embodiment, a physician 24 inserts guidewire 28 through a nose 26 of patient 22 and navigates a distal section (shown in FIG. 2 below) of guidewire 28 to the target location of the balloon, e.g., an ostium within the ENT system. After positioning the distal end of guidewire 28 at the target location, physician 24 may guide the sinuplasty balloon along guidewire 28 to the ostium.

In alternative embodiments, the medical device may comprise any other ENT tool. Several example embodiments of guidewire 28 are described in detail in FIGS. 2-4 below.

Figure 2:
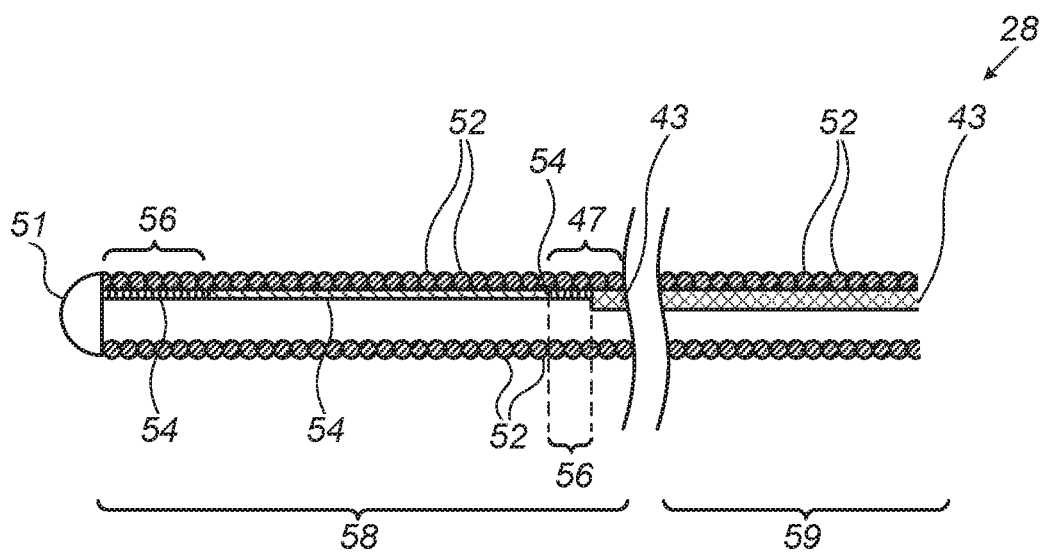
FIG. 2 is a schematic, sectional view of a guidewire, in accordance with an embodiment of the present invention.

In an embodiment, system 20 further comprises a proximal end control unit 30, which is configured to assist physician 24 in controlling and monitoring the operation of the medical device, and for navigating the distal section of guidewire 28 (shown in FIG. 2). In some embodiments, unit 30 is connected via a cable 32 to an operating console (not shown).

Methods for Improving Mechanical Strength of the Guidewire

FIG. 2 is a schematic, sectional view of guidewire 28, in accordance with an embodiment of the present invention. In some embodiments, guidewire 28 comprises a flexible spiral coil 52 made from, or coated with, a biocompatible material. In an embodiment, guidewire 28 may also be coated (e.g., between the coil surface and the biocompatible material) with a suitable radio-opaque material, so as to allow visibility of guidewire 28 while using medical imaging techniques, such as computerized tomography (CT), during an ENT procedure.

During navigation and/or when retracting guidewire 28 out of the ENT system of patient 22, the guidewire may be caught by body tissue. When the navigation and/or retraction force applied is greater than the tensile strength of coil 52, the coil may be deformed. It is important to retain the shape of coil 52 to enable smooth guidance of the medical device (e.g., balloon), to guarantee accurate navigation and patient safety during the navigation, and to allow reusing guidewire 28 in subsequent ENT procedures.

In an embodiment, a dome 51 is coupled at a tip of a distal section 58 of guidewire 28. Dome 51 is made from epoxy, such as DP270, and is configured to prevent tissue incision by the edge of wire 52. Dome 51 has a hemisphere shape (or some other suitable shape) with an exemplary diameter of 0.88 mm, which is substantially similar to an external diameter of coil 52. The actual diameter of guidewire 28 is determined depending on the medical application requirements.

In some embodiments, guidewire 28 comprises a distal section 58, and a proximal section 59 connected to unit 30. In an embodiment, a wire 43 made from nitinol or any other suitable material is coupled along the inner surface of coil 52 at proximal section 59 so as to mechanically strengthen proximal section 59 of guidewire 28. Wire 43, having a typical diameter of 0.1 mm is welded to coil 52 at a welding zone 47 located at the proximal edge (e.g., right edge in FIG. 2) of distal section 58.

In an embodiment, a fiber 54 extends along an inner surface of distal section 58 of coil 52 so as to mechanically strengthen coil 52. In an embodiment, fiber 54 may be made from a non-magnetic and non-conductive fiber having high tensile strength, such as vectran. Fiber 54 may be coupled to the inner surface of coil 52 at suitable coupling locations 56, typically by using a suitable (e.g., biocompatible) adhesive material, such as DP270 epoxy.

The tensile strength of vectran is about 3 giga-pascal (GPa) whereas the tensile strength of nitinol is about an order of magnitude lower, e.g., 200-700 mega-pascal (MPa). Therefore, using a vectran fiber having a diameter of 15-20 microns may increase the mechanical strength of distal section 58 by a factor of about 10, without compromising the guidewire flexibility, which is important for navigation and retraction of guidewire 28 in the ENT system. Vectran material is biocompatible, thermally stable at body temperatures (its melting temperature is 330° C.) and durable to radiation. Therefore vectran makes guidewire 28 reusable for ENT procedures that may further expose guidewire 28 to various conditions, such as moisture and ultraviolet (UV) radiation.

Methods for Providing Electromagnetic Shielding to the Guidewire

Figure 3:
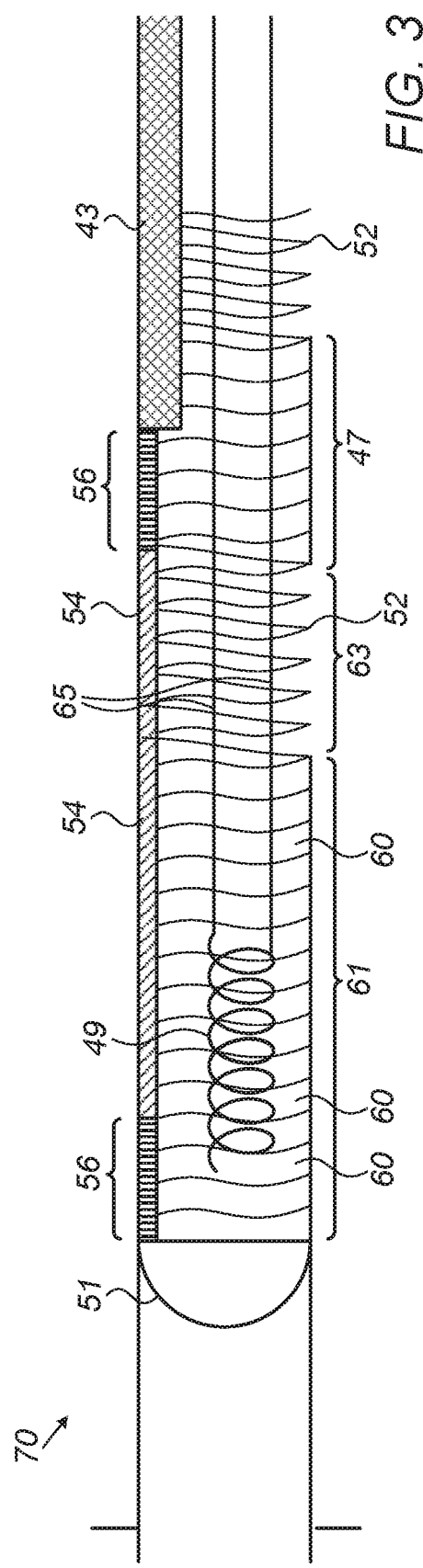
FIG. 3 is a schematic, pictorial illustration of a distal section of a guidewire, in accordance with an embodiment of the present invention.

FIG. 3 is a schematic, pictorial illustration of a guidewire distal section 70, in accordance with an embodiment of the present invention. Distal section 70 may replace, for example, distal section 58 of FIG. 2 above. In an embodiment, guidewire 28 comprises a sensor 49, such as a position sensor of a magnetic position tracking system. Sensor 49 is made from one or more metallic coils, each having a typical length of 1.5 mm and a typical diameter of 10-12 microns (the length and diameter may vary with application requirements).

In some embodiments, sensor 49 is fitted within an internal lumen of coil 52 at a zone 61. Sensor 49 may be electrically connected to unit 30 by electrical wires 65, which pass through the internal lumen of coil 52 and are configured to exchange electrical signals indicative of position between sensor 49 and the magnetic position system, via unit 30 and cable 32.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004, 2003/0120150 A1, issued as U.S. Pat. No. 7,729,742 on Jun. 1, 2010 and 2004/0068178 A1, now abandoned, whose disclosures are all incorporated herein by reference.

Sensor 49 is configured to generate position signals in response to sensed external magnetic fields from field generators (not shown) of the magnetic position system. The position signals are indicative of the position of zone 61 in the coordinate system of the position tracking system.

In some cases, undesired electromagnetic interference, such as radio-frequency (RF) waves, may interfere with the intended operation of guidewire 28. Such RF waves may interfere with the operation of the position sensor and/or with its position signal, thereby degrading the measurement accuracy of the position tracking system. Therefore, it is important to isolate wires 65 from such undesired electromagnetic interference. Nitinol is a diamagnetic material having magnetic having a permeability lower than 1.002 and susceptibility lower than that of stainless steel. Such magnetic properties may suffice for shielding wires 65, but the non-magnetic properties of vectran are preferred for isolating sensor 49.

In some embodiments, during the production of guidewire 28, a soldering material 60, such as tin may be applied to coil 52 at zone 61. In some embodiments, zone 61 may be about twice as long as sensor 49 (e.g., 2.5-3.3 mm), which is disposed within zone 61 as shown in FIG. 3. In an embodiment, material 60 is configured to (i) provide mechanical strength to the distal section, and (ii) electromagnetically isolate sensor 49 and wires 65 from undesired electromagnetic interference.

In some embodiments, the thickness and type of material 60 may determine the frequencies that will pass through material 60 in zone 61 for operating sensor 49. In some embodiments, the material composition and/or thickness of material 60 is chosen to (i) provide electromagnetic shielding at the frequency range of the undesired interference, and (ii) be substantially transparent at the frequency range of the magnetic field applied by the position tracking system. In this manner, material 60 does not impact the measurement of the desired magnetic field by sensor 49, and at the same time shields the sensor from undesired electromagnetic interference.

For example, a 200 micron thickness of tin is adapted to pass a frequency range of 17-19 kilo-hertz (KHz) produced by the magnetic position tracking system, and to block interfering frequencies, such as radio frequencies at the MHz range, typically broadcasted by commercial and other radio stations. It is important that the blocked range of frequencies (determined by the material and thickness) will not overlap with the frequency-range produced by the magnetic position tracking system.

The specification of three-dimensional (3D) positioning accuracy of sensor 49 is typically about 1 mm in each of the X/Y/Z directions. The inventors have found that by applying material 60 over zone 61, the 3D positioning accuracy of sensor 49 had been maintained within a range of 0-0.6 mm.

In an embodiment, a zone 63 that separates between zones 61 and 47 is not coated with material 60, so as to retain mechanical flexibility of guidewire 28 during navigation and retraction. In an alternative embodiment, zone 63 may be also coated with any suitable electromagnetically isolating material so as to shield wires 65 or for mechanically strengthening zone 63 (e.g., instead of or in addition to using fiber 54).

Figure 4:
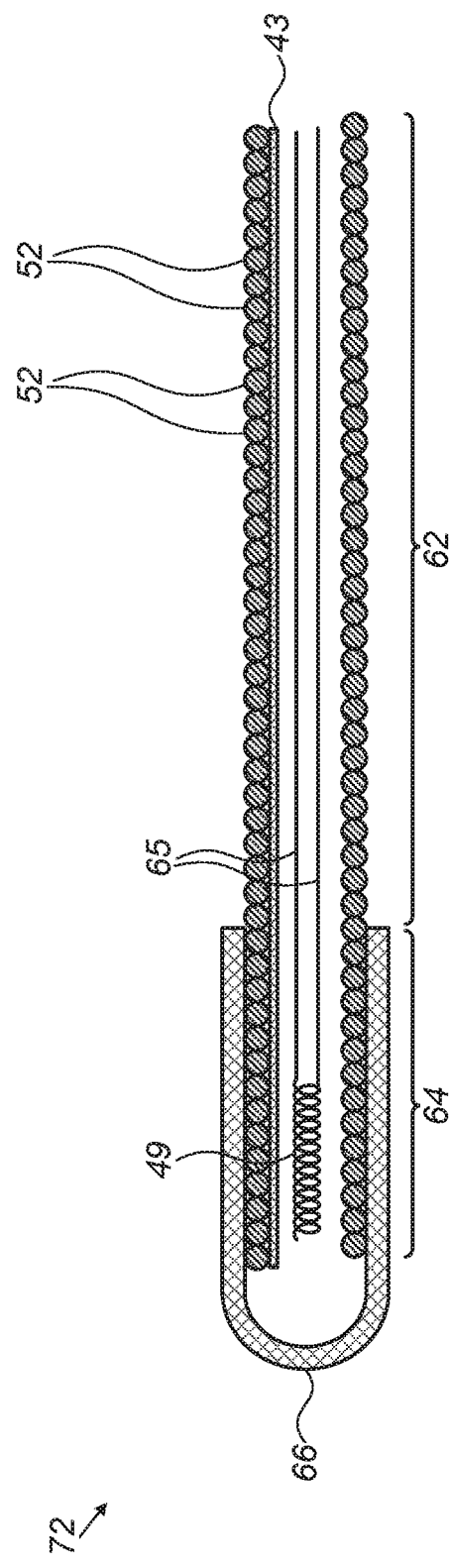
FIG. 4 is a schematic, sectional view of a distal section of a guidewire, in accordance with another embodiment of the present invention.

FIG. 4 is a schematic, sectional view of a guidewire distal section 72, in accordance with another embodiment of the present invention. Distal section 72 may replace, for example, distal section 58 of FIG. 2 above. In some embodiments, wire 43 may extend along coil 52 so as to mechanically strengthen distal section 72.

In some embodiments, a hypo tube 66, which is configured to mechanically strengthen a distal tip 64 of distal section 72, may be coupled at the distal tip. Tube 66 may overlap with wire 43, so as to strengthen the entire length of distal section 72. In an embodiment, tube 66 is made from stainless steel, such as 316SS, and has a round shape so as to prevent tissue incision by the edge of wire 52 when navigating the guidewire in the ENT system.

In an embodiment, tube 66 provides stiffness at the distal tip so that the tip is not flexible for navigating within sharp curves of the ENT system. Therefore, tube 66 should be sufficiently short, e.g., may range from 1-3.5 mm for ENT applications and may have a different length suitable for other applications.

In alternative embodiments, any other suitable strengthening element, such as fiber 54, may be used instead of wire 43.

The examples of FIGS. 2-4 refer to specific guidewire configurations. These configurations, however, are chosen purely for the sake of conceptual clarity. In alternative embodiments, the disclosed techniques can be used, mutatis mutandis, in various other types of guidewires, such as hollow guidewires that are configured to guide catheters and ENT tools through the guidewire, to the target location.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical guidewire, comprising:
    (a) a flexible spiral coil, which is configured to guide a medical device into a patient body, wherein the flexible spiral coil defines an outer surface and an inner diameter, wherein the flexible spiral coil includes:
        (i) a first portion, wherein the first portion includes a position sensor coupled to an inner surface and a coating material around the outer surface, wherein the coating material is configured to isolate the position sensor from electromagnetic signals, and
        (ii) a second portion, wherein the second portion is proximal to the first portion, wherein the second portion does not include the coating material;
    (b) a fiber, which extends along at least part of the coil in the inner diameter defined by the coil, wherein the fiber is fully contained within the inner diameter, wherein the fiber is coupled to the at least part of the coil at one or more first predefined locations in the inner diameter defined by the coil and is configured to mechanically strengthen the at least part of the coil; and
    (c) a strengthening element, which is coupled to one or more second predefined locations along a distal section of the coil, and which is configured to mechanically strengthen the distal section, wherein at least a portion of the strengthening element is distal to a distal end of the fiber, wherein the fiber extends proximally relative to the strengthening element such that a proximal portion of the fiber is positioned proximally in relation to a proximal end of the strengthening element, wherein the strengthening element is elongate and defines a length that extends along a portion of a length of the coil, wherein the length of the strengthening element is parallel with the length of the coil.

2. The medical guidewire according to claim 1, wherein the strengthening element comprises an electrically-conductive material, and is further configured to provide electromagnetic shielding that reduces electromagnetic interference to measurements of the position sensor.

3. The medical guidewire according to claim 2, wherein the position sensor is configured to sense signals in a first frequency range, and wherein the strengthening element is configured to pass the signals in the first frequency range, and to reduce the electromagnetic interference in a second frequency range that is different from the first frequency range.

4. The medical guidewire according to claim 1, wherein the strengthening element comprises a biocompatible material.

5. The medical guidewire according to claim 1, wherein at least a first location among the first predefined locations is identical to a second location among the second predefined locations, and wherein the strengthening element is configured to couple the fiber to the at least part of the coil at the first location.

6. The medical guidewire according to claim 1, wherein the strengthening element comprises a hypo-tube.

7. The medical guidewire according to claim 1, wherein the fiber is made from vectran.

8. The medical guidewire according to claim 1, wherein the strengthening element is positioned about the outer surface of the coil.

9. The medical guidewire according to claim 1, wherein the coating material includes tin.

10. A method for producing a medical guidewire, the method comprising:
    (a) providing a flexible spiral coil for guiding a medical device into a patient body, wherein the coil defines an outer surface and a hollow interior, wherein the hollow interior includes a position sensor at a distal end of the coil;
    (b) coating a first portion and a second portion of the outer surface of the coil with a coating material, wherein the coating material is configured to isolate the position sensor from electromagnetic signals, wherein a third portion longitudinally interposed between the first portion and the second portion is configured to laterally flex;
    (c) extending along at least part of the hollow interior coil a fiber that mechanically strengthens the at least part of the coil, and coupling the fiber to the at least part of the coil at one or more first predefined locations, wherein the fiber is fully contained within the hollow interior of the coil; and
    (d) coupling to one or more second predefined locations along a distal section of the coil a strengthening element for mechanically strengthening the distal section, wherein at least a portion of the strengthening element is located distal to a distal end of the fiber, wherein the fiber extends proximally relative to the strengthening element such that a proximal portion of the fiber is positioned proximally in relation to a proximal end of the strengthening element, wherein the strengthening element is elongate and defines a length that extends along a portion of a length of the coil, wherein the length of the strengthening element is parallel with the length of the coil.

11. The method according to claim 10, wherein the strengthening element comprises an electrically-conductive material, and further provides electromagnetic shielding that reduces electromagnetic interference to measurements of the position sensor.

12. The method according to claim 11, wherein the position sensor is configured to sense signals in a first frequency range, and wherein the strengthening element is configured to pass the signals in the first frequency range, and to reduce the electromagnetic interference in a second frequency range that is different from the first frequency range.

13. The method according to claim 11, wherein the electrically-conductive material comprises a biocompatible material.

14. The method according to claim 10, wherein coupling the fiber comprises coupling the fiber to an inner surface of the coil at the first predefined locations.

15. The method according to claim 10, wherein at least a first location among the first predefined locations is identical to a second location among the second predefined locations, and wherein coupling the fiber comprises coupling the fiber to the at least part of the coil at the first location.

16. The method according to claim 10, wherein the strengthening element comprises a hypo-tube.

17. The method according to claim 10, wherein the fiber is made from vectran.

18. The method according to claim 10, wherein coupling the strengthening element comprises securing the strengthening element about the outer surface of the coil.

\* \* \* \* \*